(12) United States Patent
Shelby

(10) Patent No.: US 6,931,941 B2
(45) Date of Patent: Aug. 23, 2005

(54) METHOD AND APPARATUS FOR FATIGUE TESTING

(75) Inventor: Ryan Shelby, Royal Oak, MI (US)

(73) Assignee: NHK International Corp., Wixom, MI (US)

( * ) Notice: Subject to any disclaimer, the term of this patent is extended or adjusted under 35 U.S.C. 154(b) by 0 days.

(21) Appl. No.: 10/932,080

(22) Filed: Sep. 2, 2004

(65) Prior Publication Data

US 2005/0050963 A1 Mar. 10, 2005

Related U.S. Application Data

(60) Provisional application No. 60/500,266, filed on Sep. 5, 2003.

(51) Int. Cl.$^7$ ................................................. G01N 3/32
(52) U.S. Cl. ....................................................... 73/808
(58) Field of Search .............................. 73/9, 828, 761, 73/799, 798, 809, 790, 808, 161, 862.69; 414/751; 346/139 C (56) References Cited

U.S. PATENT DOCUMENTS

| | | |
|---|---|---|
| 1,091,219 A | 3/1914 | Harvey |
| 2,222,892 A | 11/1940 | Wunderlich |
| 2,350,722 A | 6/1944 | Buckingham |
| 2,381,241 A | 8/1945 | Wilcox |
| 2,614,414 A | 10/1952 | Schafer et al. |
| 2,685,195 A | 8/1954 | Streblow |
| 2,706,404 A | 4/1955 | Schiesel |
| 2,706,907 A | 4/1955 | Cox |
| 4,346,392 A * | 8/1982 | Isobe et al. ............. 346/139 C |
| 5,033,298 A | 7/1991 | Hueck |
| 5,520,501 A * | 5/1996 | Kouno et al. ................ 414/741 |
| 5,795,990 A * | 8/1998 | Gitis et al. ......................... 73/9 |
| 6,615,640 B2 * | 9/2003 | Ahn et al. ......................... 73/9 |

FOREIGN PATENT DOCUMENTS

| | | |
|---|---|---|
| GB | 2 167 523 | 5/1986 |
| JP | 10-260122 | 9/1998 |

OTHER PUBLICATIONS

Hueck, Manfred, A New High Speed Suspension Spring Test Machine; SAE International, The Engineering Society For Advancing Mobility Land Sea Air and Space; SAE Technical Paper Series; International Congress and Exposition, Detroit, Michigan—Feb. 26–Mar. 2, 1990.

* cited by examiner

Primary Examiner—Max Noori
Assistant Examiner—Octavia Davis
(74) Attorney, Agent, or Firm—Dykema Gossett PLLC (57) ABSTRACT

A fatigue test system includes a frame having top, intermediate and bottom supports each operatively interconnected by at least one extension, and the intermediate support being disposed between the top and bottom supports. The fatigue test system further includes a driving mechanism connectable to one of the supports to drive the support substantially along a longitudinal axis of the extension for fatigue testing at least one spring disposed between the top and intermediate supports, and at least one further spring disposed between the intermediate and bottom supports. In an alternative embodiment, the fatigue test system includes a frame including top and bottom supports each interconnected by an extension, and a driving mechanism disposed between the top and bottom supports for driving springs against the top and bottom supports, each spring being fatigue tested by being driven along a longitudinal axis of the extension or a central axis of the spring.

27 Claims, 5 Drawing Sheets

METHOD AND APPARATUS FOR FATIGUE TESTING

RELATED APPLICATIONS

This application claims benefit of priority of Provisional Application Ser. No. 60/500,266 filed on Sep. 5, 2003.

BACKGROUND OF INVENTION a. Field of Invention

The invention relates generally to fatigue testing, and more particularly to a method and apparatus for fatigue testing springs and other such devices.

b. Description of Related Art

Figure 1:
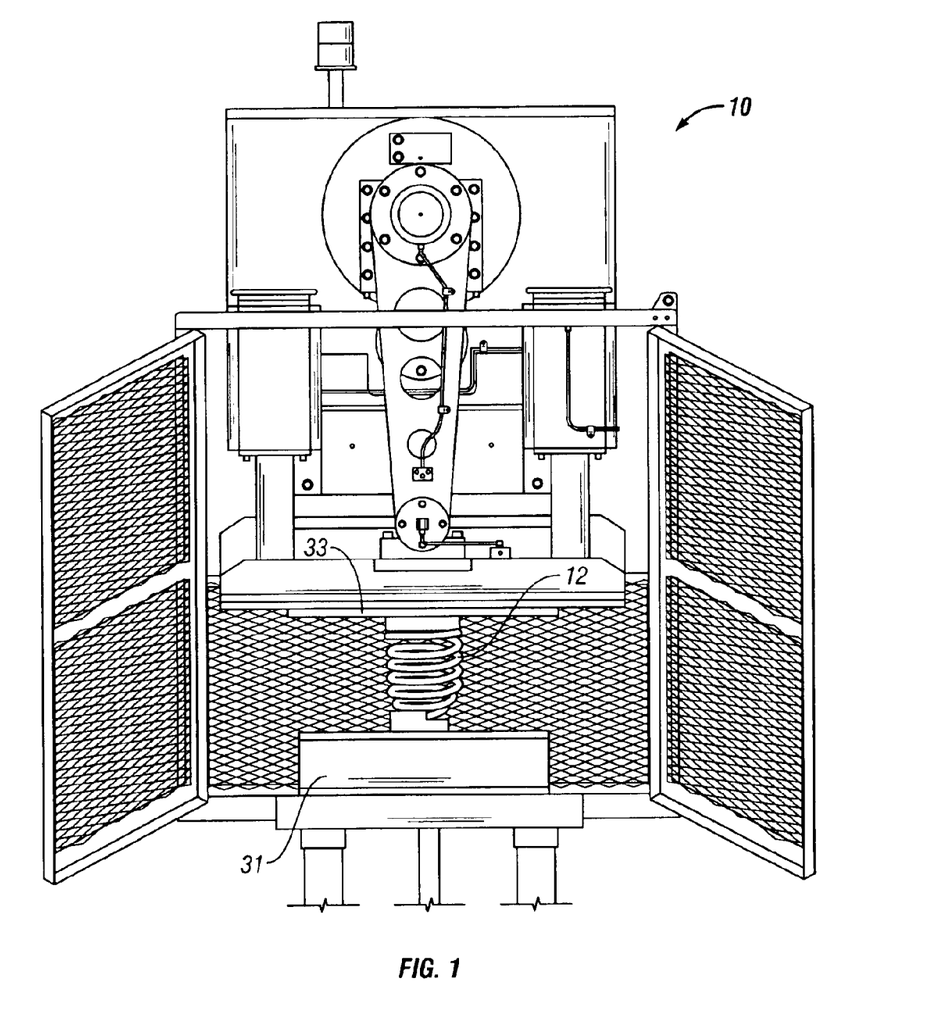
FIG. 1 is a front view illustrative of a conventional fatigue test system for fatigue testing springs and other such devices.
Figure 2:
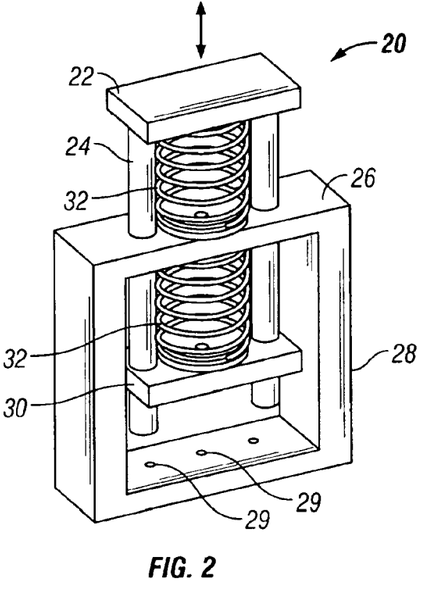
FIG. 2 is an isometric view of a first embodiment of a fatigue test system according to the present invention, the system including a fixed center.

Single story coil fatigue test systems are generally used in the art to fatigue test coil springs and other such devices. As disclosed in JP 410260122A, and further in U.S. Pat. No. 2,350,722, the disclosure of which is incorporated herein by reference, conventional spring fatigue test systems generally include a fatigue testing machine similar to the one disclosed in FIG. 1 herein. Referring to FIG. 1, conventional fatigue testing machines generally include a mechanism 10 driven into one or more mounted coil springs 12 repeatedly using hydraulic, electrical or pneumatic power until the spring fatigues, or a cycle criteria has been achieved. The force of driving mechanism 10 in such a conventional system must however be constant in order to compress spring 12 from highest (i.e. rebound) to lowest (i.e. jounce) height positions. Accordingly, the number of springs which may be tested in a conventional fatigue test system at any given time is limited primarily by the driving capacity of the system.

The prior art also includes spring fatigue testing machines for testing multiple springs in a given testing cycle. For example, as disclosed in U.S. Pat. No. 2,381,241, the disclosure of which is incorporated herein by reference, there is disclosed in FIG. 1 a circular spring testing machine for testing springs A disposed on rods 30 and compressible by rotary ring 46. While the mechanism disclosed in the '241 patent enables testing of multiple springs, it is nevertheless limited to compression as opposed to compression/tension testing of multiple springs. Moreover, due to the requirement for adjustment of numerous levers and guides, in operation, the mechanism disclosed in the '241 patent is completely impractical for high speed and repeatable spring testing, as is required in today's automotive and other mass manufacturing environments.

In an improvement to the mechanism of the '241 patent, SAE Tech Paper No. 900663 (hereinafter "SAE '663"), titled "A New High Speed Suspension Spring Test Mechanism," discloses an additional circular fatigue testing machine for testing multiple springs. For the mechanism disclosed in SAE '663, coil springs are each setup individually around a rotating cam, which compared to the mechanism of the '241 patent, pushes and pulls the various rods to compress the springs. As discussed above for the mechanism of the '241 patent, although the device of SAE '663 can test multiple springs at once, the SAE '663 mechanism also includes several drawbacks and limitations. For example, since each spring for the SAE '663 mechanism must be mounted individually, setup time for testing becomes a significant factor when testing multiple springs. Furthermore, the load savings relationship between each spring and its adjacent counterpart is hindered due to the multiple forces being applied by the other springs mounted at different angles.

Yet further, as disclosed in U.S. Pat. No. 2,222,892, the disclosure of which is incorporated herein by reference, there is disclosed in FIGS. 2 and 3 a multiple spring testing mechanism including springs 19 mounted on fixed plates 11, 21, and further mounted on oscillating beam 14. In operation, as beam 14 is oscillated by means of crank mechanism 15, 16, as discussed in Col. 2:35–38, due to the uneven oscillation in the left-most versus the right-most springs, the right-most springs tend to break faster than the left-most springs. It therefore becomes readily apparent that the fatigue testing results generated by the mechanism of the '892 patent are extremely difficult to comprehend, in that the location of the springs on the mechanism, as well as the degree of crank of mechanism 15, 16, which is adjustable at slide block 17, must be taken into account for determining the life cycle of a left-most spring, as opposed to a central or a right-most spring.

It would therefore be of benefit to provide a fatigue test system with increased capacity of testing the compression and tension cycles of springs and other such devices, without increasing the force needed to drive the springs. It would also be of benefit to provide a fatigue test system which can reduce the overall driving force needed per test cycle, which can favorably eliminate any resistance to the driving mechanism that may be produced by the springs during neutral conditions, and for which the testing technique and results are repeatable and simple to interpret. There thus remains a need for a fatigue test system, which is robust in design, efficient to operate, simple to assemble and disassemble, and which is economically feasible to manufacture and utilize.

SUMMARY OF INVENTION

The invention solves the problems and overcomes the drawbacks and deficiencies of conventional fatigue test system designs by providing a fatigue test system having increased capacity of testing the compression and tension cycles of springs and other such devices.

Thus, an exemplary aspect of the present invention is to provide a fatigue test system with increased capacity of testing springs and other such devices without increasing the force needed to drive the springs.

Another aspect of the present invention is to provide a fatigue test system which reduces the overall driving force needed per test cycle, and which favorably eliminates any resistance to the driving mechanism that may be produced by the springs during neutral conditions.

The present invention achieves the aforementioned exemplary aspects by providing a fatigue test system including a frame having top, intermediate and bottom supports each operatively interconnected by at least one extension, and the intermediate support being disposed between the top and bottom supports. The fatigue test system may further include a driving mechanism connectable to one of the supports to drive the support substantially along a longitudinal axis of the extension for fatigue testing at least one spring disposed between the top and intermediate supports, and at least one further spring disposed between the intermediate and bottom supports.

For the fatigue test system disclosed above, at least one of the supports may be adjustably disposed along the extension for adjusting a distance between adjacently disposed supports. The extension may be a shaft disposed through suitable openings in the intermediate support. The intermediate support may be fixed to the frame for permitting movement of the top and bottom supports by means of the driving mechanism, or alternatively, may be movable relative to the top and bottom supports.

The invention yet further provides a frame including top, intermediate and bottom supports each operatively interconnected by at least one extension. The intermediate support may be disposed between the top and bottom supports. The frame may further include a driving mechanism connectable to one of the supports to drive the support substantially along a central axis of at least two springs disposed between the top and intermediate supports, and at least two further springs disposed between the intermediate and bottom supports for fatigue testing the springs by substantially uniformly compressing the springs.

For the fatigue test system described above, at least one of the supports may be adjustably disposed along the extension for adjusting a distance between adjacently disposed supports. The extension may be a shaft disposed through suitable openings in the intermediate support. The intermediate support may be fixed to the frame for permitting movement of the top and bottom supports by means of the driving mechanism, or alternatively, may be movable relative to the top and bottom supports.

The invention yet further provides a method for fatigue test a plurality of springs. The method includes providing a frame including top, intermediate and bottom supports each operatively interconnected by at least one extension, the intermediate support being disposed between the top and bottom supports. The method may further include connecting a driving mechanism to one of the supports to drive the support substantially along a central axis of at least two springs disposed between the top and intermediate supports, and at least two further springs disposed between the intermediate and bottom supports for fatigue testing the springs by substantially uniformly compressing the springs. The method may alternatively include connecting a driving mechanism to one of the supports to drive the support substantially along a longitudinal axis of the extension for fatigue testing at least two springs disposed between the top and intermediate supports, and at least two further springs disposed between the intermediate and bottom supports.

For the method described above, the method may further include adjusting at least one of the supports along the extension for adjusting a distance between adjacently disposed supports. The extension may be a shaft disposed through suitable openings in the intermediate support. The method may further include fixing the intermediate support to the frame for permitting movement of the top and bottom supports by means of the driving mechanism, or alternatively, moving the intermediate support relative to the top and bottom supports.

For an alternative embodiment of the fatigue test system disclosed above, the invention provides a fatigue test system including a frame including top and bottom supports each operatively interconnected by at least one extension. The system further includes a driving mechanism disposed between the top and bottom supports for driving at least one spring against the top support, and further driving at least one further spring against the bottom support, each spring being fatigue tested by being driven substantially along a longitudinal axis of the extension.

For the fatigue test system described above, the driving mechanism may be operatively mounted to the extension. At least one of the top and bottom supports may be adjustably disposed along the extension for permitting adjustment of a distance of the adjustably disposed support from the driving mechanism. The extension may be a shaft disposed through an opening in at least one of the top and bottom supports.

The invention yet further provides a fatigue test system including a frame including top and bottom supports each operatively interconnected by at least one extension. The system further includes a driving mechanism disposed between the top and bottom supports for driving at least one spring against the top support, and further driving at least one further spring against the bottom support, each spring being fatigue tested by being substantially uniformly compressed along a central axis thereof.

For the fatigue test system described above, the driving mechanism may be operatively mounted to the extension. At least one of the top and bottom supports may be adjustably disposed along the extension for permitting adjustment of a distance of the adjustably disposed support from the driving mechanism. The extension may be a shaft disposed through an opening in at least one of the top and bottom supports.

The invention also provides a method for fatigue testing a plurality of springs, the method including providing a frame including top and bottom supports each operatively interconnected by at least one extension. The method further includes connecting a driving mechanism between the top and bottom supports to drive at least one spring against the top support, and further drive at least one further spring against the bottom support, each spring being fatigue tested by being substantially uniformly compressed along a central axis thereof, or alternatively, by being driven substantially along a longitudinal axis of the extension.

For the method described above, the method may further include operatively mounting the driving mechanism to the extension. At least one of the top and bottom supports may be adjustably disposed along the extension for permitting adjustment of a distance of the adjustably disposed support from the driving mechanism. The extension may be a shaft disposed through an opening in at least one of the top and bottom supports.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings.

DETAILED DESCRIPTION OF THE PREFERRED EMBODIMENTS

Referring now to the drawings wherein like reference numerals designate corresponding parts throughout the several views, FIGS. 2–5, 6–8 and 9–11 respectively illustrate first to third embodiments of fatigue test systems (hereinafter "system") according to the present invention, generally designated 20, 100, 200, respectively.

Specifically, as illustrated in FIGS. 2–5, the first embodiment of system 20 may include an upper plate 22 fixedly connectable to a driving mechanism, such as mechanism 10 illustrated in FIG. 1, of a conventional fatigue test system, such as at 33. System 20 may include at least two extensions, illustrated as circular shafts 24 in FIG. 2, disposed within suitable openings (not shown) in top wall 26 of frame 28. The openings in top wall 26 may include suitable bearings (not shown) for permitting smooth reciprocation of shafts 24 therein. It should be noted that shafts 24 may be formed of a variety of cross-sections for permitting reciprocation of plates 22, 30 therewith. Frame 28 may include a plurality of fixing points 29 for fixing frame 28 to reaction mass 31 (see FIG. 1). Shafts 24 may be fixedly mounted to lower plate 30 at or adjacent their bottom-most ends thereof. Lower plate 30 may include a retention means such as a pin (not shown), ball-screw locking mechanism (not shown) or suitable fastening means disposed on a threaded section thereof for permitting vertical adjustability and retention thereof along the length of shaft 24 for testing springs 32 of different heights. It should be noted that plates 22, 30 may be formed of a variety of cross-sections for supporting springs 32. In the case of pins, shafts 24 may be provided with a plurality of spaced holes (not shown) for permitting suitable pins to be inserted therethrough for retaining lower plate 30 at predetermined heights along the length thereof. In the case of fastening means, shafts 24 may include a threaded section of a predetermined length so as to permit suitable nuts or other fastening means to be threadedly engaged thereon for retaining lower plate 30 at a predetermined height. Those skilled in the art would appreciate in view of this disclosure that a variety of alternative retention techniques may be used for retaining lower plate 30 at a predetermined height along the length of shafts 24, without departing from the scope of the present invention.

Figure 3:
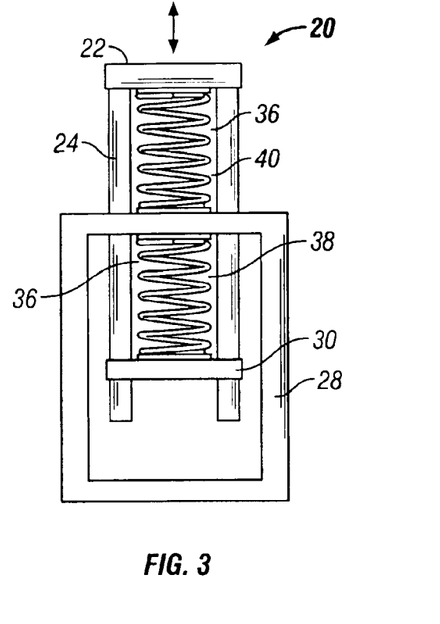
FIG. 3 is a front view of the fatigue test system of FIG. 2, illustrating both springs at normal (i.e. center) position.
Figure 4:
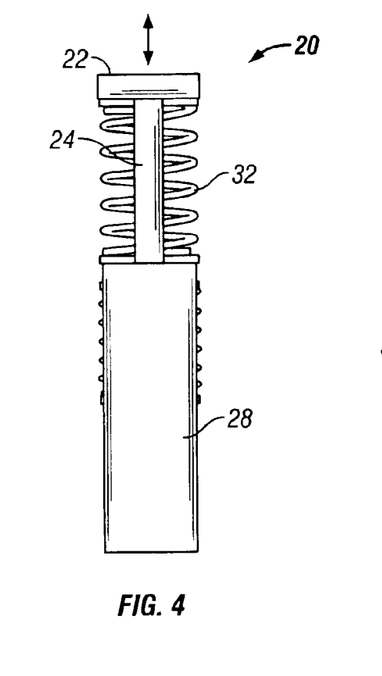
FIG. 4 is a side view of the fatigue test system of FIG. 3.
Figure 5:
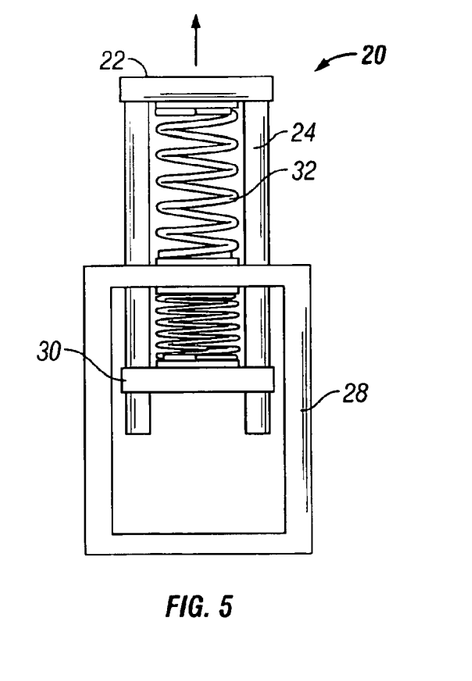
FIG. 5 is a front view of the fatigue test system of FIG. 2, illustrating the top spring at rebound and the bottom spring at jounce.

In order to test springs 32, the springs may be removably mounted in their normal (center) position within areas 36 to upper and lower plates 22, 30, respectively, and top wall 26, in the configuration illustrated in FIG. 3. With a driving mechanism, such as mechanism 10 of FIG. 1, connected to plate 22 to push plate 22 downwards and likewise pull plate 22 upwards for each cycle of mechanism 10, springs 32 may be fatigue testes as needed. Specifically, with the downward movement of plate 22, while the upper spring is placed in compression, the lower spring is placed in tension, and vice-versa, as illustrated in FIG. 5. Fatigue testing springs 32 in the manner illustrated in FIGS. 2–5 therefore doubles the capacity of a conventional fatigue test system by utilizing the energy of each spring to assist in the testing of the oppositely mounted spring. It should also be noted that system 20 doubles the capacity of a conventional fatigue test system without increasing the amount of force needed to drive each spring during each cycle.

System 20 of the present invention also reduces the overall force needed to drive each spring during each cycle, since as driving mechanism 10 compresses each mounted story 38, 40, the remaining force of the opposite mounted story is eliminated from the overall force required of the driving mechanism. In essence, the compressive and tensile forces of each spring 32 are used to assist in the fatigue testing of the respective tensile and compressive forces of the oppositely mounted spring. Lastly, system 20 provides for the elimination of any resistance to driving mechanism 10 that generally occurs in conventional fatigue test systems when the mounted springs are in their neutral condition. For example, as illustrated in FIG. 3, assuming both springs 32 are mounted equally, system 20 will therefore experience a zero (0) force condition at the neutral position since the force of story 38, for example, applied to system 20 is cancelled by the opposite force of story 40 when driving mechanism 10 is at the center of the cycle. It should be noted that for the fatigue test system described above, driving mechanism 10 may alternatively be mounted to lower plate 30 instead of upper plate 22 as needed.

The second embodiment of system 100 will now be described in detail in reference to FIGS. 6–8.

Figure 6:
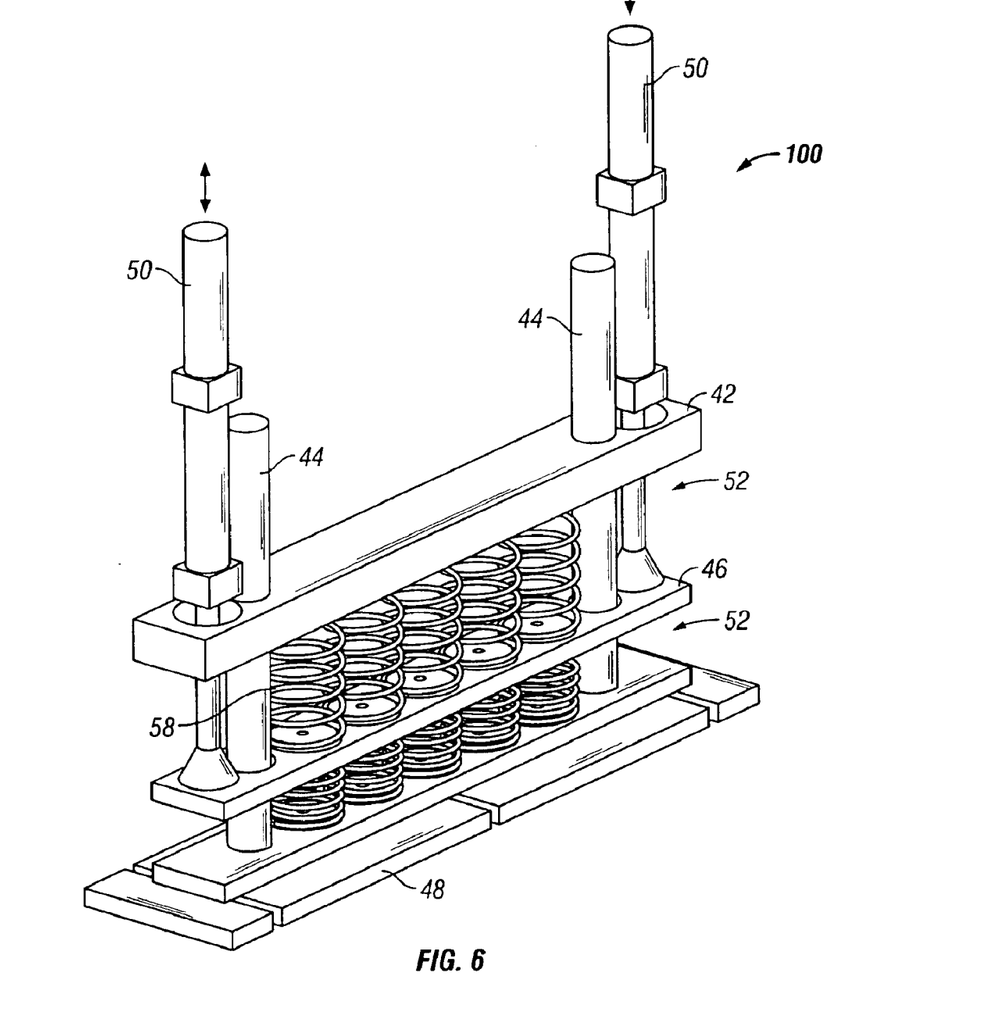
FIG. 6 is an isometric view of a second embodiment of a fatigue test system according to the present invention, the system including a movable center.
Figure 7:
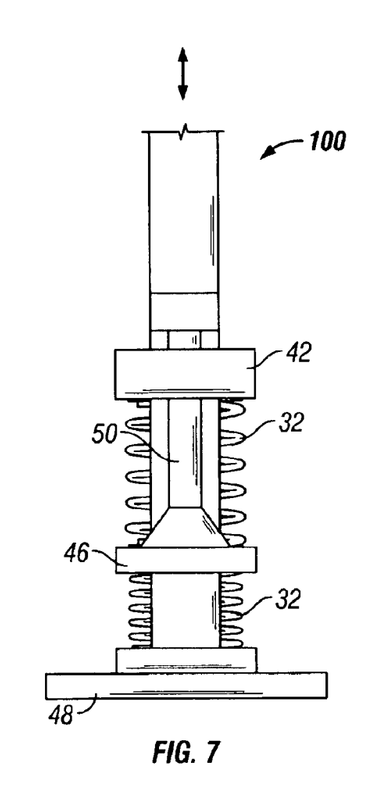
FIG. 7 is a side view of the fatigue test system of FIG. 6.
Figure 8:
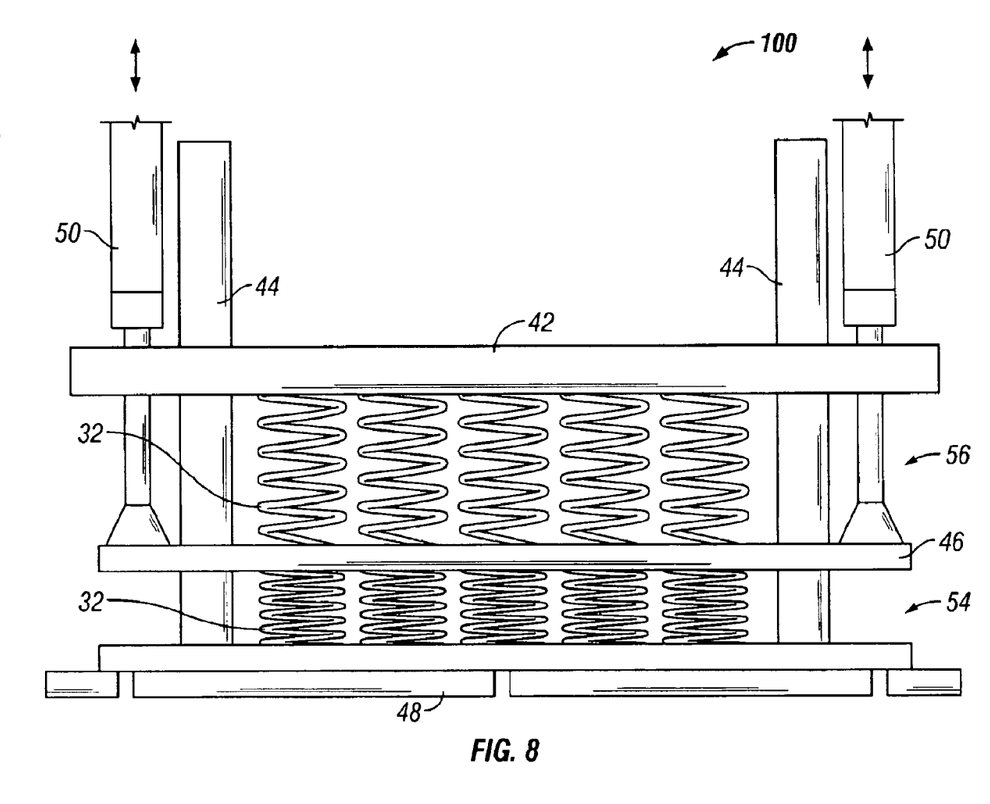
FIG. 8 is a front view of the fatigue test system of FIG. 6, illustrating the top spring at rebound and the bottom spring at jounce.

Specifically, for the second embodiment of system 100, as illustrated in FIGS. 6–8, system 100 may include a vertically fixable plate 42 connectable to a driving mechanism 10 of a conventional fatigue test system, such as the system disclosed in FIG. 1. System 100 may include shafts 44 disposed within suitable openings in plate 42 and movable plate 46. Shafts 44 may be fixedly mounted to lower fixing plate 48. As discussed above for the first embodiment of system 20, for the second embodiment of system 100, it should be noted that shafts 44 may be formed of a variety of cross-sections for permitting reciprocation of plate 46 by means of driving mechanism 10. Plate 42 may include a retention means such as a pin (not shown), ball-screw locking mechanism (not shown) or suitable fastening means disposed on a threaded section thereof for permitting vertical adjustability and retention thereof along the length of shafts 44 for insertion and testing of springs 58 of different heights. Driving mechanism 10 may include members 50 disposed within suitable openings in plate 42 and fixedly connected to plate 46, or alternatively, may be directly connected to plate 46 by a connection (not shown) disposed adjacent plate 46, instead of through plate 42. As also discussed above for the first embodiment of system 20, for the second embodiment of system 100, it should be noted that plates 42, 46, 48 may be formed of a variety of cross-sections for supporting springs 58.

In order to test springs 58, the springs may be removably mounted within areas 52. With driving mechanism 10 connected to plate 46 to push plate 46 downwards and likewise pull plate 46 upwards for each cycle of mechanism 10, springs 58 may be fatigue testes as needed. In a similar manner to fatigue test system 20, fatigue testing springs 58 in the manner illustrated in FIGS. 6–8 likewise doubles the capacity of a conventional fatigue test system by utilizing the energy of each spring to assist in the testing of the oppositely mounted spring. It should also be noted that as discussed above for fatigue test system 20, system 100 doubles the capacity of a conventional fatigue test system without increasing the amount of force needed to drive each spring during each cycle.

System 100 of the present invention also reduces the overall force needed to drive each spring during each cycle, since as driving mechanism 10 compresses each mounted story 54, 56, the remaining force of the opposite mounted story is eliminated from the overall force required of the driving mechanism. As discussed above for the first embodiment of fatigue test system 20, for system 100, the compressive and tensile forces of each spring 58 are used to fatigue test the respective tensile and compressive forces of the oppositely mounted spring. Lastly, system 100 provides for the elimination of any resistance to driving mechanism 10 that generally occurs in conventional fatigue test systems when the mounted springs are in their neutral condition. For example, as illustrated above for the first embodiment for FIG. 3, assuming both springs 58 are mounted equally, system 100 will therefore experience a zero (0) force condition at the neutral position since the force of story 54, for example, applied to system 100 is cancelled by the opposite force of story 56 when driving mechanism 10 is at the center of the cycle.

The third embodiment of system 200 will now be described in detail in reference to FIGS. 9–11.

Figures 9, 10, 11:
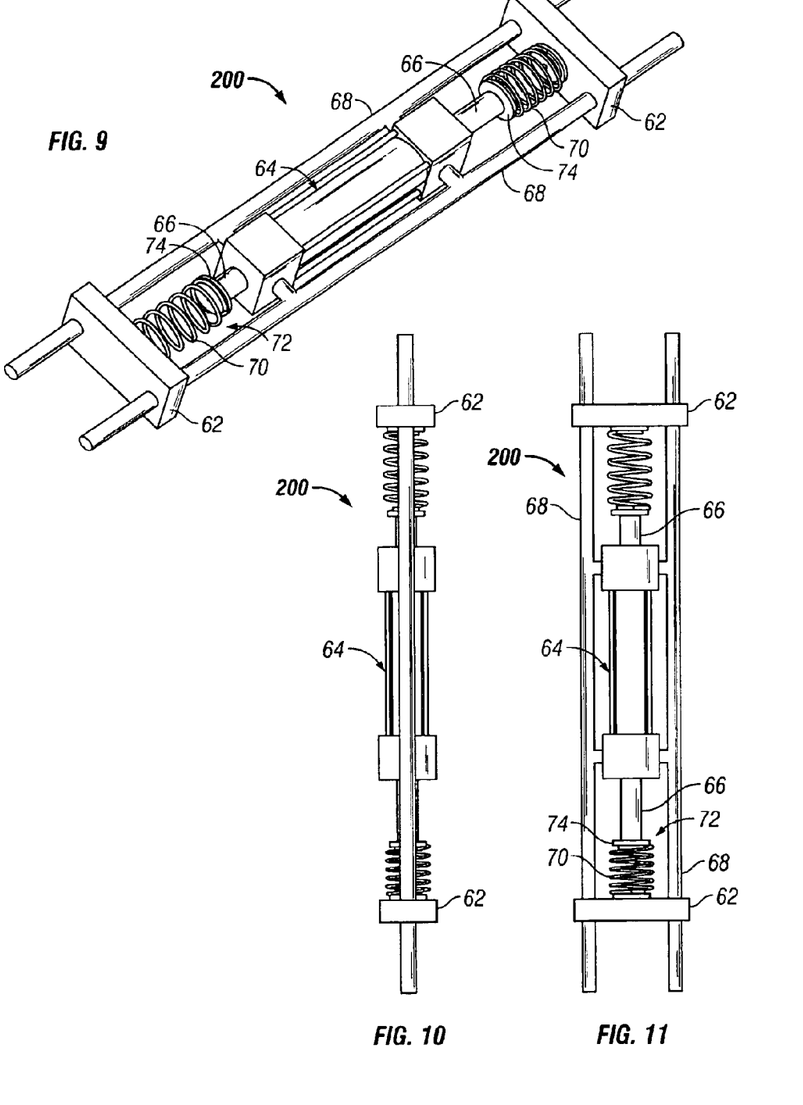
FIG. 9 is an isometric view of a third embodiment of a fatigue test system according to the present invention, the system including an integrated actuator assembly.
FIG. 10 is a side view of the fatigue test system of FIG. 9.
FIG. 11 is a front view of the fatigue test system of FIG. 9, illustrating the top spring at rebound and the bottom spring at jounce.

Specifically, for the third embodiment of system 200, as illustrated in FIGS. 9–11, system 200 may include plates 62 slidably disposed on shafts 68, and a driving mechanism 64, such as a driving mechanism of a MTS actuator, having a piston (not shown) including piston rods 66. Shafts 68 may be disposed within suitable openings in plates 62, in a similar manner as shafts 44 of the second embodiment of system 100. As discussed above for the first and second embodiments of systems 20, 100, for the third embodiment of system 200, it should be noted that shafts 68 may be formed of a variety of cross-sections for permitting sliding movement of plates 62 for insertion of springs 70. Plates 62 may each include a retention means such as a pin (not shown), ball-screw locking mechanism (not shown) or suitable fastening means disposed on a threaded section thereof for permitting sliding movement and lockable retention thereof along the length of shafts 68, for permitting insertion and testing of springs 70 of different heights. As also discussed above for the first and second embodiments of systems 20, 100, for the third embodiment of system 200, it should be noted that plates 62 may be formed of a variety of cross-sections for supporting springs 70.

In order to test springs 70, the springs may be removably mounted within areas 72. With piston rods 66 of driving mechanism 64 having mounting plates 74 affixed thereto for mounting springs 70, with springs 70 mounted within areas 72 as shown in FIG. 9, plates 74 may be reciprocated back and forth in the direction of shafts 68 to fatigue test springs 70 as needed. In a similar manner to fatigue test systems 20 and 100, fatigue testing springs 70 in the manner illustrated in FIGS. 9–11 likewise doubles the capacity of a conventional fatigue test system by utilizing the energy of each spring to assist in the testing of the oppositely mounted spring. It should also be noted that as discussed above for fatigue test systems 20, 100, system 200 doubles the capacity of a conventional fatigue test system without increasing the amount of force needed to drive each spring during each cycle.

System 200 of the present invention also reduces the overall force needed to drive each spring during each cycle, since the compressive and tensile forces of each spring 70 are used to fatigue test the respective tensile and compressive forces of the oppositely mounted spring. Lastly, system 200 provides for the elimination of any resistance to driving mechanism 64 that generally occurs in conventional fatigue test systems when the mounted springs are in their neutral condition. For example, as illustrated above for the first embodiment for FIG. 3, assuming both springs 70 are mounted equally, system 200 will therefore experience a zero (0) force condition at the neutral position since the force of the first spring 70 is cancelled by the force of the second spring 70 mounted opposite to driving mechanism 64 when driving mechanism 64 is at the center of the cycle. Those skilled in the art will appreciate in view of this disclosure that although only two springs 70 are shown for testing with system 200, if needed, a wider plate (not shown) may be attached to the end of piston rods 66 to replace plates 74 and thereby increase the number of springs which may be mounted and tested by system 200.

The present invention thus provides a fatigue test system having increased capacity of testing the compression and tension cycles of springs and other such devices, without increasing the force needed to drive the springs. Moreover, the present invention also provides a fatigue test system which reduces the overall driving force needed per test cycle, and which favorably eliminates any resistance to the driving mechanism that may be produced by the springs during neutral conditions.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims.

What is claimed is:

1. A fatigue test system comprising:
    a frame including top, intermediate and bottom supports each operatively interconnected by at least one extension, said intermediate support being disposed between said top and bottom supports; and
    a driving mechanism connectable to one of said supports to drive said support substantially along a longitudinal axis of said extension for fatigue testing at least one spring disposed between said top and intermediate supports, and at least one further spring disposed between said intermediate and bottom supports.

2. A fatigue test system according to claim 1, wherein at least one of said supports being adjustably disposed along said extension for adjusting a distance between adjacently disposed supports.

3. A fatigue test system according to claim 1, wherein said extension being a shaft disposed through an opening in said intermediate support.

4. A fatigue test system according to claim 1, wherein said intermediate support being fixed to said frame for permitting movement of said top and bottom supports by means of said driving mechanism.

5. A fatigue test system according to claim 1, wherein said intermediate support being movable relative to said top and bottom supports.

6. A fatigue test system comprising:
    a frame including top, intermediate and bottom supports each operatively interconnected by at least one extension, said intermediate support being disposed between said top and bottom supports; and
    a driving mechanism connectable to one of said supports to drive said support substantially along a central axis of at least two springs disposed between said top and intermediate supports, and at least two further springs disposed between said intermediate and bottom supports for fatigue testing said springs by substantially uniformly compressing said springs.

7. A fatigue test system according to claim 6, wherein at least one of said supports being adjustably disposed along said extension for adjusting a distance between adjacently disposed supports.

8. A fatigue test system according to claim 6, wherein said extension being a shaft disposed through an opening in said intermediate support.

9. A fatigue test system according to claim 6, wherein said intermediate support being fixed to said frame for permitting movement of said top and bottom supports by means of said driving mechanism.

10. A fatigue test system according to claim 6, wherein said intermediate support being movable relative to said top and bottom supports.

11. A method for fatigue testing a plurality of springs, said method comprising:
   providing a frame including top, intermediate and bottom supports each operatively interconnected by at least one extension, said intermediate support being disposed between said top and bottom supports; and, one of:
   connecting a driving mechanism to one of said supports to drive said support substantially along a central axis of at least two springs disposed between said top and intermediate supports, and at least two further springs disposed between said intermediate and bottom supports for fatigue testing said springs by substantially uniformly compressing said springs, and
   connecting a driving mechanism to one of said supports to drive said support substantially along a longitudinal axis of said extension for fatigue testing at least two springs disposed between said top and intermediate supports, and at least two further springs disposed between said intermediate and bottom supports.

12. A method according to claim 11, further comprising adjusting at least one of said supports along said extension for adjusting a distance between adjacently disposed supports.

13. A method according to claim 11, wherein said extension being a shaft disposed through suitable openings in said intermediate support.

14. A method according to claim 11, further comprising fixing said intermediate support to said frame for permitting movement of said top and bottom supports by means of said driving mechanism.

15. A method according to claim 11, further comprising moving said intermediate support relative to said top and bottom supports.

16. A fatigue test system comprising:
   a frame including top and bottom supports each operatively interconnected by at least one extension; and
   a driving mechanism disposed between said top and bottom supports for driving at least one spring against said top support, and further driving at least one further spring against said bottom support, each spring being fatigue tested by being driven substantially along a longitudinal axis of said extension.

17. A fatigue test system according to claim 16, wherein said driving mechanism is operatively mounted to said extension.

18. A fatigue test system according to claim 16, wherein at least one of said top and bottom supports being adjustably disposed along said extension for permitting adjustment of a distance of said adjustably disposed support from said driving mechanism.

19. A fatigue test system according to claim 16, wherein said extension being a shaft disposed through an opening in at least one of said top and bottom supports.

20. A fatigue test system comprising:
   a frame including top and bottom supports each operatively interconnected by at least one extension; and
   a driving mechanism disposed between said top and bottom supports for driving at least one spring against said top support, and further driving at least one further spring against said bottom support, each spring being fatigue tested by being substantially uniformly compressed along a central axis thereof.

21. A fatigue test system according to claim 20, wherein said driving mechanism is operatively mounted to said extension.

22. A fatigue test system according to claim 20, wherein at least one of said top and bottom supports being adjustably disposed along said extension for permitting adjustment of a distance of said adjustably disposed support from said driving mechanism.

23. A fatigue test system according to claim 20, wherein said extension being a shaft disposed through an opening in at least one of said top and bottom supports.

24. A method for fatigue testing a plurality of springs, said method comprising:
   providing a frame including top and bottom supports each operatively interconnected by at least one extension; and
   connecting a driving mechanism between said top and bottom supports to drive at least one spring against said top support, and further drive at least one further spring against said bottom support, each spring being fatigue tested by one of:
      being substantially uniformly compressed along a central axis thereof, and
      being driven substantially along a longitudinal axis of said extension.

25. A method according to claim 24, further comprising operatively mounting said driving mechanism to said extension.

26. A method according to claim 24, wherein at least one of said top and bottom supports being adjustably disposed along said extension for permitting adjustment of a distance of said adjustably disposed support from said driving mechanism.

27. A method according to claim 24, wherein said extension being a shaft disposed through an opening in at least one of said top and bottom supports.

* * * * *